(12) United States Patent
Kruecker et al.

(10) Patent No.: US 8,734,349 B2
(45) Date of Patent: May 27, 2014

(54) SYSTEM AND METHOD FOR QUANTITATIVE 3D CEUS ANALYSIS

(75) Inventors: Jochen Kruecker, Washington, DC (US); Sheng Xu, Rockville, MD (US)

(73) Assignee: Koninklijke Philips N.V., Eindhoven (NL)

( * ) Notice: Subject to any disclaimer, the term of this patent is extended or adjusted under 35 U.S.C. 154(b) by 791 days.

(21) Appl. No.: 12/740,004

(22) PCT Filed: Nov. 5, 2008

(86) PCT No.: PCT/IB2008/054620
§ 371 (c)(1),
(2), (4) Date: Apr. 27, 2010

(87) PCT Pub. No.: WO2009/063361
PCT Pub. Date: May 22, 2009

(65) Prior Publication Data
US 2010/0256495 A1 Oct. 7, 2010

Related U.S. Application Data

(60) Provisional application No. 61/045,307, filed on Apr. 16, 2008, provisional application No. 60/987,796, filed on Nov. 14, 2007.

(51) Int. Cl.
*A61B 8/00* (2006.01)
(52) U.S. Cl.
USPC .......................................................... 600/437
(58) Field of Classification Search
USPC ........................................ 600/437, 441, 458
See application file for complete search history.

(56) References Cited

U.S. PATENT DOCUMENTS 5,538,004 A * 7/1996 Bamber ........................ 600/443
5,743,266 A 4/1998 Levene et al.
(Continued)

FOREIGN PATENT DOCUMENTS

WO WO2006107801 10/2006

OTHER PUBLICATIONS

Edward A. Gardner et al., "Removing Local Motion From Ultrasonic Images Using Nonaffine Registration for Contrast Quantification," IEEE Int'l Ultrasonics, Ferroelectrics, and Frequency Control Conf., pp. 1718-1721, 2004.

(Continued)

*Primary Examiner* — Tse Chen
*Assistant Examiner* — Rochelle Reardon (57) ABSTRACT

A method (50) for quantitative 3D contrast enhanced ultrasound (CEUS) analysis includes acquiring (54) an initial pair of ultrasound contrast and tissue images of an anatomy. A region of interest (ROI) or volume of interest (VOI) is established (56) in the initial acquired tissue image, which becomes the baseline tissue image. The established ROI/VOI is automatically registered (58) from the initial tissue image to the initial contrast image, which becomes a baseline contrast image. Quantitative analysis is performed (60) on the ROI/VOI of the baseline contrast image. The method further includes acquiring (62) a next ultrasound contrast and tissue image pair, corresponding to an i th current contrast and tissue image pair. Frame-to-frame registration is established (64) between (i) the current tissue image and (ii) the baseline tissue image, the frame-to-frame registration being used (66) between the current tissue image and the baseline tissue image to transfer the ROI/VOI from (i) the baseline contrast image to (ii) the current contrast image, thereby creating a transformed ROI/VOI in the current contrast image. Quantitative analysis is then performed (68) on the transformed ROI/VOI of the current contrast image.

19 Claims, 4 Drawing Sheets

(56) References Cited

U.S. PATENT DOCUMENTS

| | | | |
|---|---|---|---|
| 6,416,477 B1* | 7/2002 | Jago | 600/447 |
| 7,603,182 B2* | 10/2009 | Sano et al. | 700/15 |
| 2006/0239585 A1 | 10/2006 | Valadez et al. | |
| 2007/0055161 A1* | 3/2007 | Garg et al. | 600/458 |
| 2007/0167801 A1 | 7/2007 | Webler et al. | |

OTHER PUBLICATIONS

M. Krix, "Quantification of perfusion of liver tissue and metastases using a multivessel model for replenishment kinetics of ultrasound contrast agents," Ultrasound in medicine & biology, vol. 30, pp. 1355-1363, 2004.

J. Kruecker, et al., "Electromagnetic needle tracking and multi-modality imaging for biopsy and ablation guidance," in Int J Cars, Berlin, Germany, 2007, pp. 147-150.

S. Xu, et al., "Real-time Motion Tracking Using 3D Ultrasound," Proc. SPIE vol. 6509, 65090X (Mar. 21, 2007).

S. Mule, et al., "An Original Methodology for Quantitative Assessment of Perfusion in Small Animal Studies Using Contrast-Enhanced Ultrasound", Engineering in Medicine and Biology Society, 2007, EMBS 2007, 29th Annual International Conference of the IEEE, Piscataway, NJ,, pp. 347-350 (Aug. 1, 2007).

* cited by examiner

SYSTEM AND METHOD FOR QUANTITATIVE 3D CEUS ANALYSIS

CROSS REFERENCE TO RELATED CASES

Applicants claim the benefit of International Application Number PCT/IB2008/054620, filed Nov. 5, 2008, U.S. Provisional Application Ser. No. 61/045,307, filed Apr. 16, 2008 and U.S. Provisional Application Ser. No. 60/987,796, filed Nov. 14, 2007.

The present embodiments relate generally to ultrasound systems and more particularly, to a method and apparatus for quantitative 3D contrast enhanced ultrasound analysis.

Quantitative analysis of localized, transient effects in contrast-enhanced ultrasound (CEUS) imaging is currently difficult and tedious because of respiratory (and other) tissue motion, requiring manual identification of the desired region of interest (ROI) or volume of interest (VOI) in each individual ultrasound frame.

Contrast enhanced ultrasound (CEUS) imaging refers to ultrasound imaging after intra-venous injection of an ultrasound contrast agent (such as Definity®, Bristol-Myers Squibb). On modern ultrasound scanners, specific imaging modes have been implemented to take advantage of the non-linear acoustic response of contrast agents, thus only highlighting tissue with contrast uptake. The resulting image is called "contrast image" and has a very different appearance compared to non-contrast images. It is also possible to image tissue after contrast injection in regular grayscale mode. In the later instance, the resulting image is called the "tissue image" and looks similar to grayscale images obtained without contrast injection, showing only a small enhancement in areas of contrast uptake.

The transient visualization of contrast (e.g. inflow/outflow) can provide valuable information about local tissue perfusion that may be used to differentiate benign and malignant masses. However, tissue motion (e.g. due to respiration) makes it necessary to manually identify the desired ROI in each ultrasound frame. Thus, the analysis is disadvantageously time consuming, user-dependent, and can only be carried out retrospectively, which precludes use of the transient CEUS information for guidance of biopsy or therapeutic procedures.

Accordingly, an improved method and system for overcoming the problems in the art is desired.

In the figures, like reference numerals refer to like elements. In addition, it is to be noted that the figures may not be drawn to scale.

An apparatus and method for acquiring contrast-enhanced ultrasound (CEUS) data uses image-based registration to compensate automatically and in real time for tissue motion. The CEUS image and the corresponding tissue image are acquired essentially simultaneously and automatically registered, i.e. a region of interest (ROI) or volume of interest (VOI) defined in one image outlines the same tissue in the other image. The tissue image will not change (or change only to a small extent) during the contrast administration, and can thus be used to register the current image to the baseline image in which the ROI or VOI was identified. The ultrasound probe may be integrated with an external position tracking device, providing a framework to use the quantitative CEUS information directly for navigation and guidance of biopsy and localized therapy. The invention enables automatic, quantitative analysis of transient contrast imaging parameters. As a result, the manual identification of an ROI or VOI in each individual ultrasound frame, which is difficult and tedious because of respiratory (and other) tissue motion, but required by current methods of analysis, becomes no longer necessary for each ultrasound frame of a series of frames.

According to one embodiment of the present disclosure, a system and method for quantitative CEUS analysis acquire CEUS data such that tissue motion can be compensated for automatically and in real-time. This enables automatic, quantitative analysis of transient contrast imaging parameters. In addition, the system provides a framework in which the results of such a quantitative analysis can be immediately used for guidance of biopsy or therapeutic procedures.

According to the further embodiments of the present disclosure, a system and method for quantitative CEUS analysis (a) automatically compensates for tissue motion, allowing automatic analysis of the ROI or VOI, the ROI or VOI having been identified in a single ultrasound frame alone, the single ultrasound frame corresponding to a baseline tissue image, as will be discussed further herein, and (b) integrates with an interventional procedure (e.g., a biopsy) or localized therapy guidance system to provide target information based on the results of the CEUS analysis.

The embodiments of the present disclosure overcome the manual and time-consuming identification of ROIs/VOIs in each frame of a transient CEUS acquisition, and thereby overcome the current limitation of transient CEUS to retrospective analysis. With CEUS acquisition, a transient contrast effect may develop over several minutes, thereby easily requiring identification of greater than one thousand (>1000) ROIs/VOIs in a time series acquired at 10 Hz. The embodiments of the present disclosure advantageously address such a problem with use of image-based registration, in spite of the fact that image-based registration of transient CEUS images is difficult and non-robust because of the low information content and frame-to-frame variability of the CEUS image.

The embodiments of the present disclosure advantageously overcome this problem by use of simultaneously acquiring the CEUS image with a corresponding tissue image, as discussed further herein. Within a given time duration of the contrast administration, certain characteristics of the tissue image do not change (or will only change by a non-appreciable extent) during the contrast administration, and can thus be used to register a current contrast image to a baseline tissue image in which the ROI was identified. In addition, since tissue and contrast images are acquired simultaneously or near-simultaneously, the corresponding tissue and contrast images are automatically registered, i.e. an ROI defined in one image outlines the very same tissue in the other image, as will be discussed further herein.

In addition, the embodiments of the present disclosure further include integrating an ultrasound probe with an external position tracking device. The integration of the ultrasound probe with the external position tracking device advantageously enables compensating for freehand motion of the probe during CEUS acquisition, thus further enhancing the robustness of the image-based registration, and reducing the dimensionality of the search space (since respiratory-induced motion of an ROI can typically be approximated by translate-only transformations). Furthermore, the integration with an external position tracking device provides a framework to use the quantitative CEUS information directly for navigation and guidance of an interventional procedure (e.g., a biopsy) and/or localized therapy.

Figure 1:
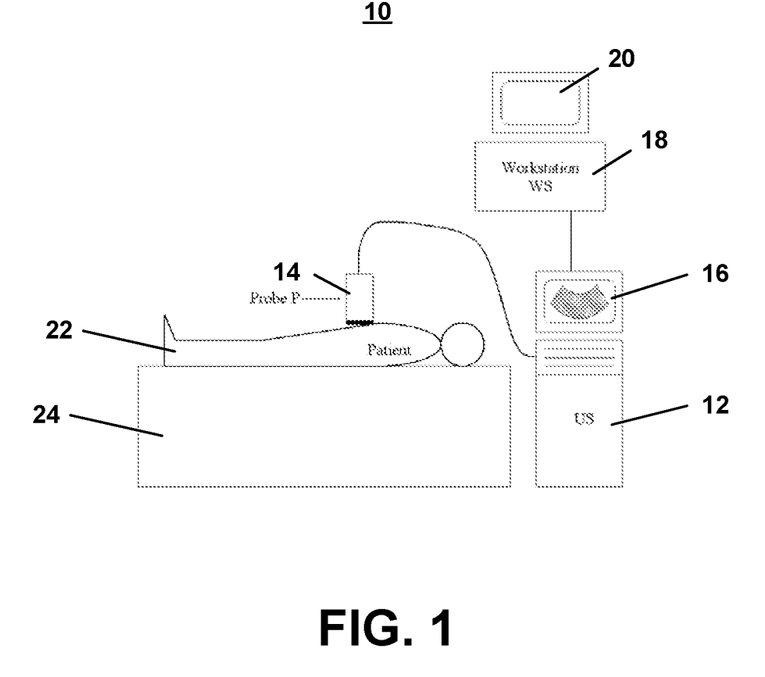
FIG. 1 is a block diagram view of a system for quantitative CEUS analysis according to one embodiment of the present disclosure.

Turning now to the drawings, FIG. 1 is a block diagram view of a system 10 for quantitative CEUS analysis according to one embodiment of the present disclosure. System 10 comprises an ultrasound scanner (US) 12 equipped and/or coupled with an ultrasound imaging probe 14. In one embodiment, the ultrasound scanner 12 comprises, for example, an iU22 ultrasound scanner commercially available from Philips Medical Systems. Imaging probe 14 comprises any suitable 3D imaging probe. In addition, ultrasound scanner 12 includes a scanner display 16. Furthermore, ultrasound scanner 12 is configured for simultaneous acquisition of contrast and tissue images. Ultrasound scanner 12 is further configured for transferring images in real-time, for example, via data streaming, to an external workstation 18. For example, transferring images in real-time can be accomplished using an iU22 ultrasound scanner with Digital Navigation Link software.

Referring still to FIG. 1, workstation 18 includes a workstation display 20. In addition, workstation 18 includes software loaded in a memory thereof, the software including instructions executable by a processor of the workstation to (i) store simultaneously acquired (and thus automatically registered) contrast and tissue images, (ii) allow manual identification of an ROI or VOI in one acquired tissue image, wherein the corresponding tissue image with the identified ROI or VOI is subsequently referred to as the "baseline image", (iii) register the image information within the ROI/VOI in the baseline image to subsequent tissue images to determine the ROI/VOI motion $T_i$ from the baseline image to the $i^{th}$ tissue image, where T is a transformation describing the corresponding translation and rotation or higher-order (non-rigid) transformation parameters, (iv) apply the same transformation $T_i$ to transform the baseline ROI/VOI into the $i^{th}$ contrast image frame, thus determining the ROI or VOI for the $i^{th}$ contrast image, hereafter denoted $ROI^i$ ($VOI^i$), and (v) perform quantitative analysis of the image contents within $ROI^i$ ($VOI^i$) in the $i^{th}$ contrast frame. The software can further include instructions executable by the processor of the workstation 18 to (vi) analyze an entire times series of quantitative results from the individual frames to determine parameters that can provide diagnostic information. Performing quantitative analysis can include, but not be limited to, computing the mean and standard deviation of brightness, etc. of the image contents within the $ROI^i$ ($VOI^i$) in the $i^{th}$ contrast frame. In addition, diagnostic information parameters determined from the analysis of the time series of quantitative results can include, but are not limited to, tissue perfusion constants, etc.

In operation, the ultrasound scanner 12, probe 14, and workstation 18 are used with a patient 22 having an anatomy that is subject to a given ultrasound diagnosis and/or a corresponding treatment or medical procedure, wherein the patient 22 is positioned upon a patient table 24. Ultrasound scanner 12 is configured to acquire contrast and tissue images in a "side by side mode", corresponding to an interleaved acquisition of contrast and tissue frames, and sends both acquired images to the workstation 18. Software is executed by workstation 18 to accommodate the following workflow.

In one embodiment, the workflow includes performing manual identification of a VOI in one acquired tissue image, wherein the corresponding tissue image becomes a "baseline image" for purposes of the method of quantitative analysis as discussed herein. The VOI can be defined by a sphere, ellipsoid, or any other user-defined 3D geometric shape. In one embodiment, the general VOI is described as a set of points on the shape surface, connected by lines to neighboring points, and grouped into triangles describing surface patches of the shape, such that the "inside" and "outside" of the VOI can be easily determined. The image information inside and in the vicinity of the VOI in the baseline tissue image is stored as a tissue template $I^{VOI}_{base}$ for subsequent image-based registration. The corresponding image information inside the VOI in the contrast image $I^{VOI}_{contrast,0}$ is quantitatively analyzed (e.g. calculating mean brightness, standard deviation of brightness etc.) for assessment of the transient contrast effect. The result(s) are stored as a set of M features $p^k_0$, where k= 1 ... M is the feature index, and the lower index denotes frame number. In this example, the baseline is immediately before contrast injection. The contrast agent is then administered to the patient.

For subsequent sets of contrast/tissue images (i.e., subsequent contrast and tissue image pairs), the baseline tissue template $I^{VOI}_{base}$ is registered to the current tissue image, resulting in a transformation $T_i$ describing the motion of the template from the baseline tissue image to the $i^{th}$ tissue image frame in image coordinates. The transformation $T_i$ comprises a rotate/translate or higher-order (non-rigid) transformation and can be computed in real-time. The same transformation $T_i$ is applied to the shape describing the VOI, resulting in $VOI^i$. The transformed $VOI^i$ outlines the same tissue in the $i^{th}$ tissue frame as the VOI outlined in the baseline tissue image. In addition, given the simultaneous (or near-simultaneous) acquisition of contrast and tissue images for the $i^{th}$ frame, the corresponding contrast and tissue images are automatically registered to one another and an ROI/VOI defined in one image outlines the exact same tissue in the other image. The image information contained within the $VOI^i$ of the $i^{th}$ contrast image, $I^{VOIi}_{contrast,i}$, is then analyzed as discussed herein above, resulting in the set of features $p^k_i$, k=1 ... M, for the $i^{th}$ frame.

The method continues by repeating registration and analysis steps for all subsequent image frames until an interruption of the acquisition occurs. Interruption of the acquisition may include, for example, a system user interruption or other system initiated interruption. Such an interruption would typically occur after the contrast effect has disappeared from the VOI. In addition, the set of features $p^k_i$ for all frames i can now be used directly to quantify tissue perfusion in the selected VOI, using suitable methods. For example, one method to quantify tissue perfusion of a selected VOI is disclosed by M. Krix, "Quantification of perfusion of liver tissue and metastases using a multivessel model for replenishment kinetics of ultrasound contrast agents," *Ultrasound in medicine & biology*, vol. 30, pp. 1355-1363, 2004.

Figure 2:
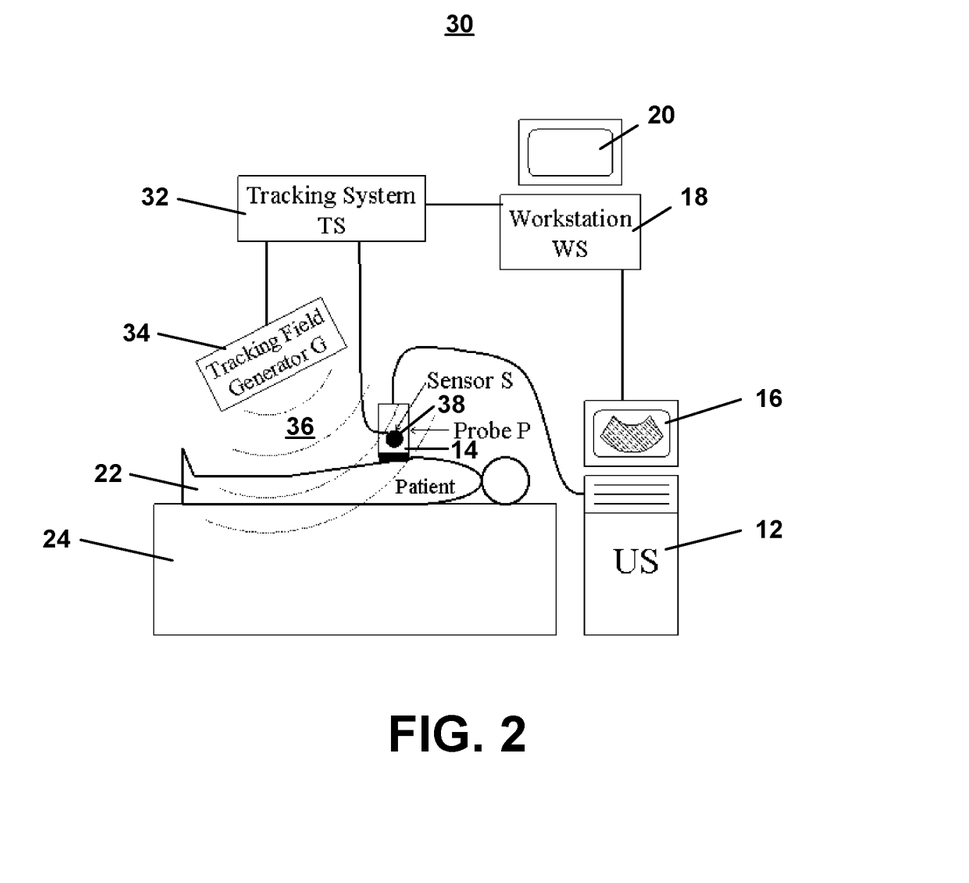
FIG. 2 is a block diagram view of a system for quantitative CEUS analysis utilizing position tacking according to another embodiment of the present disclosure.

FIG. 2 is a block diagram view of a system for quantitative CEUS analysis utilizing position tacking according to another embodiment of the present disclosure. The embodiment of FIG. 2 is similar to that of FIG. 1, with the following differences. In the embodiment of FIG. 2, the system 30 is enhanced by integration with an external position tracking system (TS) 32. The external position tracking system 32 includes a tracking field generator 34 which is configured for producing a tracking field, generally designated by reference numeral 36. A sensor 38 is coupled to the ultrasound probe 14, wherein responsive to the sensor being located within a range of sensing field 36, the sensor's position and orientation can be tracked by the tracking system 32. In one embodiment, workstation 18 is coupled to tracking system 32 and configured to communicate tracking information and/or provide tracking instructions between workstation 18 and tracking system 32 according to the requirements of a given quantitative CEUS analysis implementation. Tracking system 32 can comprise any suitable tracking system, for example, such as the electro-magnetic "Aurora" system by Northern Digital Inc., of Waterloo, Canada.

As disclosed herein, system 30 comprises an integration which provides a number of advantages. A first advantage is that the system 30 enhances a robustness of the image-based registration according to the embodiments of the present disclosure. For example, inadvertent or deliberate probe motion in freehand operation of the scanner can create big differences in the image contents of consecutive frames, thereby making it difficult to estimate the corresponding apparent ROI/VOI motion $T_i$. However, using the position/orientation of probe 14 as measured with the tracking system 32 provides for an improved starting point for the image-based registration process, enabling the ROI/VOI in the baseline image and $i^{th}$ image frame to be brought closer together at the beginning of the corresponding registration process.

A second advantage is that system 30 reduces the dimensionality of the search space. That is, the ROI motion secondary to respiration is typically well approximated by translations (i.e., no rotations). Rotational ultrasound probe motion, however, may introduce rotation in the apparent frame-to-frame motion of the ROI. By eliminating the rotational component using probe tracking, the image-based registration can be confined to three (3) degrees of freedom (DOF) corresponding to a translation in (x,y,z) instead of six (6) degrees of freedom corresponding to translation (x,y,z) and rotation ($\theta x, \theta y, \theta z$).

Another advantage of the system 30 is that the tracking system 32 provides a framework for subsequent navigation/guidance to a target identified using the quantitative ROI analysis according to the method embodiments of quantitative CEUS analysis of the present disclosure. Guidance can be provided by a fusion of the real-time ultrasound with a pre-acquired 3D image (such as CT or MRI), and/or by spatially tracking interventional or surgical devices equipped with miniaturized tracking sensors (See for example, reference JVIR 2007: Jochen Krücker, Sheng Xu, Neil Glossop, Anand Viswanathan, Jörn Borgert, Heinrich Schulz, and Bradford J. Wood. Electromagnetic tracking for thermal ablation and biopsy guidance: Clinical evaluation of spatial accuracy. JVIR, vol. 18, pp. 1141-1150, 2007).

In addition to the functionality discussed herein with reference to the system 10 of FIG. 1, in the system 30 of FIG. 2, the workstation 18 further includes software loaded in a memory thereof, the software including instructions executable by a processor of the workstation to: (i) process tracking position information from the tracking system (TS) 32 simultaneously with an image stream from the US scanner 12; (ii) store a pose $T_{base}$ of the ultrasound probe during baseline image acquisition, and for each subsequent image i, compute the pose difference $T_{base}{}^i$ between the current frame i and the baseline image; (iii) use $T_{base}{}^i$ to determine $T_i{}^0$, wherein $T_i{}^0$ corresponds to the ROI pose difference in the $i^{th}$ frame compared to baseline under the assumption of no tissue motion (i.e. the apparent motion introduced solely by moving the probe relative to the tissue); and (iv) use $T_i{}^0$ as a starting position for the image-based registration process for determining the corresponding ROI/VOI motion $T_i$ in the $i^{th}$ frame.

Figure 3:
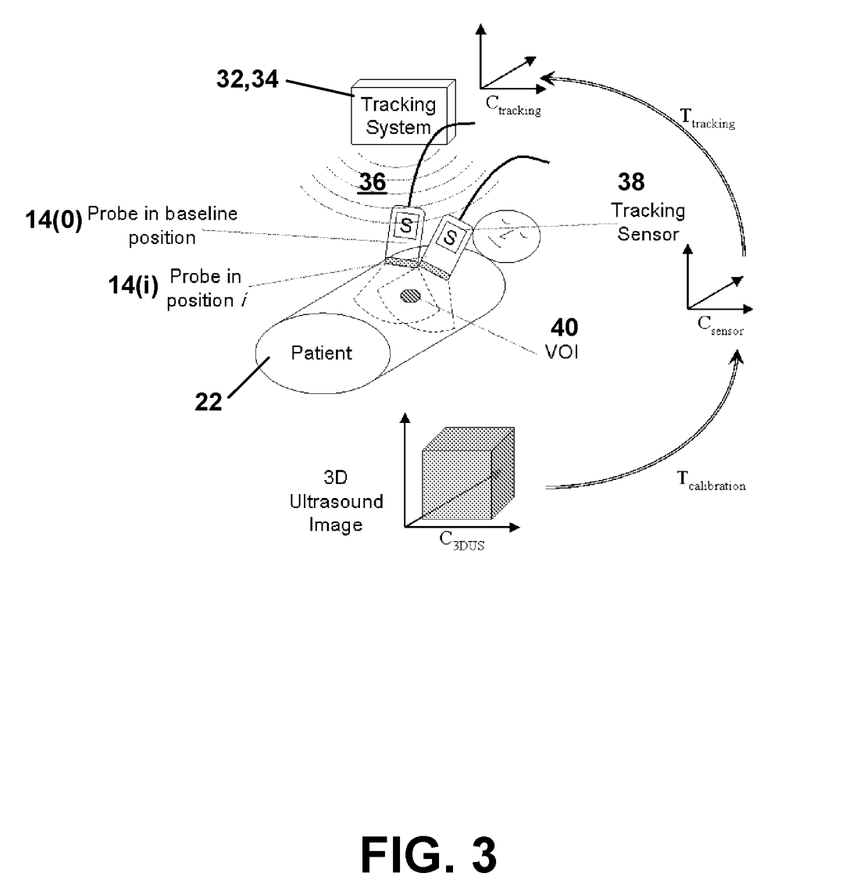
FIG. 3 is a partial block diagram view illustrating transformations between various portions of the system for quantitative CEUS analysis of FIG. 2, according to embodiments of the present disclosure.

In system 30 of the embodiment of FIG. 2, an external position tracking system (TS) 32, such as the electro-magnetic "Aurora" system (Northern Digital Inc., Waterloo, Canada) is set up next to the patient 22. A 6 degree-of-freedom (6 DoF) position sensor (S) 38 is coupled to the ultrasound probe 14, and the tracking field generator 34 is positioned such that the probe position can be tracked with tracking field 36. Tracking system 32 could also include an optical tracking system, in which tracking field generator 34 comprises a camera, for optically tracking the ultrasound probe 14 within a tracking field 36 corresponding to an optical field of view. FIG. 3 is a partial block diagram view illustrating transformations between various portions of the system for quantitative CEUS analysis of FIG. 2, according to embodiments of the present disclosure. In particular, FIG. 3 is an illustration of transformations between the coordinate systems of a 3D ultrasound image, the tracking sensor attached to the probe, and the tracking system. In one embodiment, FIG. 3 illustrates the relationship of transformations between the 6 DoF position sensor, the tracking system, and the corresponding ultrasound frame.

The transformation $T_{tracking}$ describes the current position and orientation ("pose") of the tracking sensor 14 relative to the tracking system (32,34). In other words, the transformation $T_{tracking}$ describes the relationship between the coordinate system of tracking system $C_{tracking}$ and the coordinate system of the tracking sensor $C_{sensor}$. The transformation $T_{tracking}$ is provided by the tracking system and is sent to the workstation 18 in realtime. The transformation $T_{calibration}$ describes the relationship between the coordinate system $C_{3DUS}$ of the 3D ultrasound image (i.e., voxel coordinates) and the coordinate system $C_{sensor}$ of the tracking sensor 38 attached to the probe 14. The transformation $T_{calibration}$ is determined in a one-time calibration procedure and remains fixed for a given tracking sensor 38 rigidly attached to the ultrasound probe 14.

The tracking information from the tracking sensor (S) 38 provides a starting point for image-based registrations in the following manner. The initial VOI, as indicated by reference numeral 40 in FIG. 3, and as obtained by the ultrasound probe 14 being in a baseline position 14(0), is defined in 3D ultrasound image (3DUS) voxel coordinates in the baseline image, and the corresponding tracking pose $T_{base}$ of the baseline image is stored (for example, by tracking system 32 or in suitable storage of workstation 18). For each subsequent image, for example, obtained with probe 14 being in a subsequent position 14(i), the method includes computing the transformation $T_i{}^0$ (i.e. the apparent image motion introduced solely by moving the probe relative to the tissue) using the expression given by:

$$T_i{}^0 = T_{calibration}{}^{-1} \cdot T_{tracking,i}{}^{-1} \cdot T_{base} \cdot T_{calibration}$$

where $T_{tracking,i}$ is the tracking pose of the $i^{th}$ image frame, and where the exponent $^{-1}$ indicates matrix inversion.

$T_i{}^0$ can now be used as a starting position for the image-based registration process that will determine $T_i$ as defined above. In addition, the image-based registration can now be reduced to a translation-only search since the potential rotational component (e.g., introduced by probe rotation) has been eliminated.

Figure 4:
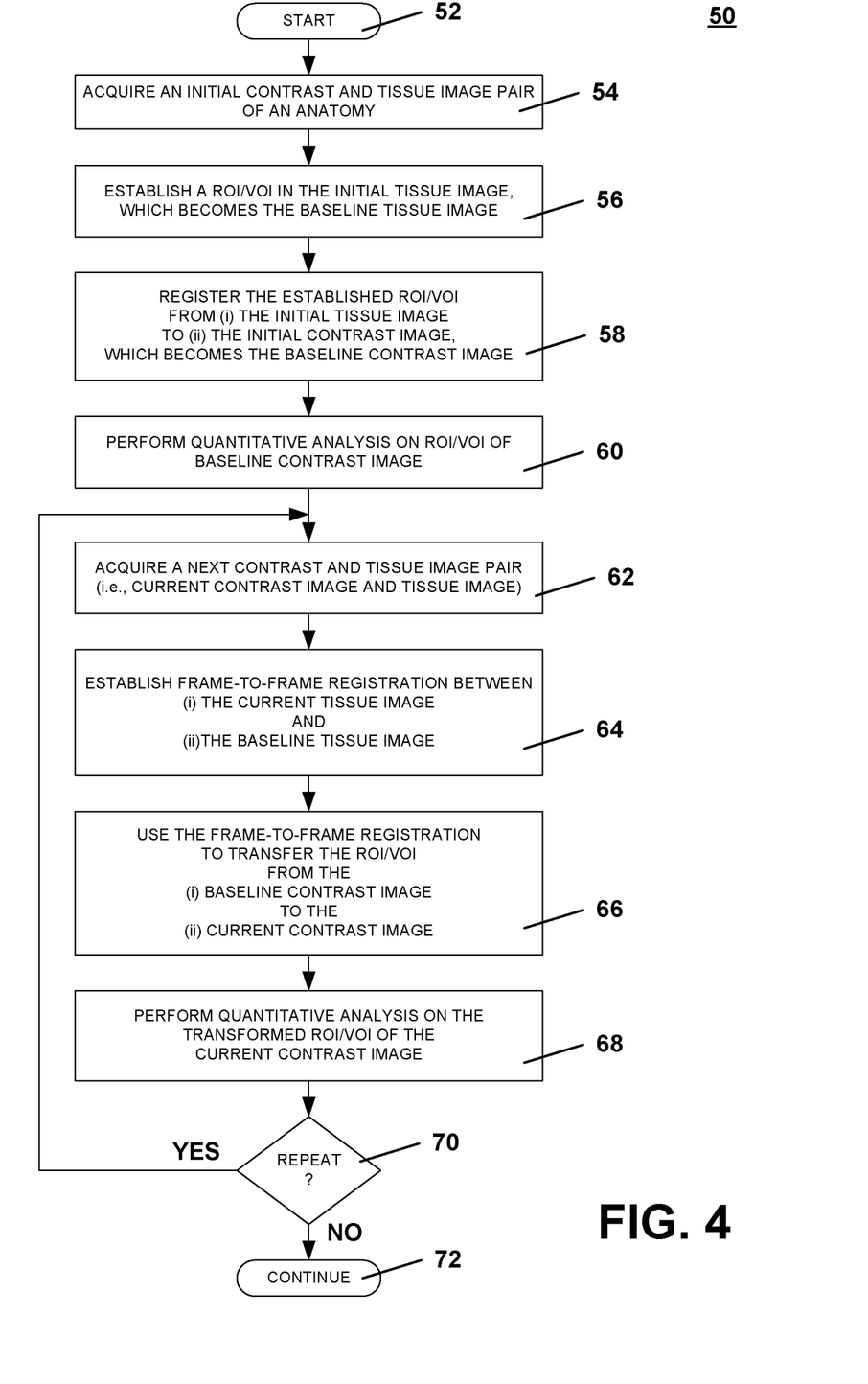
FIG. 4 is a flow diagram view illustrating a method of quantitative CEUS analysis according to another embodiment of the present disclosure.

FIG. 4 is a flow diagram view illustrating a method 50 of quantitative CEUS analysis according to another embodiment of the present disclosure. The method 50 begins at step 52 which can comprise any suitable action for initiating the method, as may be appropriate for the requirements of a given quantitative CEUS analysis. Following the start at step 52, the method proceeds to step 54. In step 54, an initial contrast and tissue image pair are acquired for a desired portion of a given anatomy. The initial contrast and tissue image pair may comprise any image pair selected for purposes of the quantitative CEUS analysis as an initial image, which does not necessarily imply that the image pair has to comprise the first image pair obtained by the system. In step 56, a ROI/VOI is established in the initial acquired tissue image. The tissue image which is used to establish the ROI/VOI then becomes the "baseline" tissue image. Establishing the ROI/VOI in the initial acquired tissue image can include manually establishing the ROI/VOI. Other methods of establishing the ROI/VOI in the initial acquired tissue image are also contemplated, for example, via suitable image processing configured to detect a given region or volume of interest within the tissue image. In step 58, the established ROI/VOI from the initial tissue image is automatically registered to the initial contrast image, and the corresponding contrast image becomes the "baseline" contrast image. As previously discussed, since the tissue image and the corresponding contrast image are acquired simultaneously (or near-simultaneously), they are automatically registered with one another, i.e. a region of interest (ROI) or volume of interest (VOI) defined in the tissue image outlines the same ROI or VOI in the contrast image. In step 60, quantitative analysis is performed on the ROI/VOI of the baseline contrast image.

In step 62, the method acquires a next contrast and tissue image pair, corresponding to a current contrast and tissue image pair. The current contrast and tissue image pair are acquired simultaneously (or near-simultaneously), wherein the current contrast image and the current tissue image are automatically registered with one another. In step 64, the method includes establishing frame-to-frame registration between (i) the current tissue image and (ii) the baseline tissue image. As noted herein, the tissue image typically has more information content than a corresponding contrast image that can be used for registration, and thus advantageously enables image-based frame-to-frame registration between the current tissue image frame and the baseline tissue image frame (in comparison to direct frame-to-frame registration between a current contrast image and the baseline contrast image). In step 66, the frame-to-frame registration between the current tissue image frame and the baseline tissue image frame is used to transfer the ROI/VOI from (i) the baseline contrast image to (ii) the current contrast image. Upon transforming the ROI/VOI of the baseline contrast image to the current contrast image, the method includes in step 68 performing quantitative analysis on the transformed ROI/VOI of the current contrast image. In another embodiment, step 66 could transform the ROI/VOI from a current contrast image to the baseline contrast image. In addition, in one embodiment, the registration and processing can be in real-time. In another embodiment, all image (and tracking) data could be acquired first and then processing for registration and quantitative analysis could be performed.

In step 70, the method queries whether to repeat the process with acquisition of a next contrast and tissue image pair. If the process is to repeat, then the method goes to step 62 and proceeds as discussed herein above. Otherwise, if the portion of the method for acquisition of subsequent contrast and tissue image pairs of CEUS quantitative analysis is finished, then the method proceeds to step 72. Step 72 represents further steps which may be carried out in accordance with the requirements of a given CEUS quantitative analysis implementation or application. For example, step 72 may include further processing for a contrast-enhanced ultrasound imaging study. Step 72 may also include further processing relating to an integration of diagnosis and therapy, for example, by providing target information and guidance for biopsy and/or therapeutic procedures.

By now it will be appreciated that a method has been disclosed for quantitative 3D contrast enhanced ultrasound (CEUS) analysis that comprises acquiring an initial ultrasound contrast and tissue image pair for a desired portion of a given anatomy. A region of interest (ROI) or volume of interest (VOI) is established in the initial acquired tissue image, wherein the corresponding tissue image becomes a baseline tissue image. The established ROI or VOI from the initial tissue image is automatically registered to the initial contrast image, wherein the corresponding contrast image becomes a baseline contrast image. Quantitative analysis is performed on the ROI or VOI of the baseline contrast image. A next ultrasound contrast and tissue image pair is acquired, corresponding to an $i^{th}$ current contrast and tissue image pair. After acquisition of the next ultrasound contrast and tissue image pair, frame-to-frame registration is established between (i) the current tissue image and (ii) the baseline tissue image. The frame-to-frame registration between the current tissue image frame and the baseline tissue image frame is used to transfer the ROI or VOI from (i) the baseline contrast image to (ii) the current contrast image, thereby creating a transformed ROI or VOI in the current contrast image. Quantitative analysis is then performed on the transformed ROI or VOI of the current contrast image. In one embodiment, acquiring the initial contrast and tissue image pair comprises acquiring the tissue image prior to acquiring of the contrast image.

According to another embodiment, the initial contrast and tissue image pair can comprise any image pair selected for purposes of the quantitative CEUS analysis as an initial image pair, which does not necessarily imply that the image pair has to comprise the first image pair obtained. In another embodiment, establishing the ROI or VOI in the initial acquired tissue image comprises manually identifying the ROI or VOI within the baseline tissue image. In a further embodiment, the step of acquiring the initial contrast and tissue image pair includes acquiring the contrast image and the tissue image simultaneously or near-simultaneously in a manner that the contrast and tissue images are automatically registered with one another. As a result, the ROI or VOI defined in the baseline tissue image outlines the same ROI or VOI in the baseline contrast image. Furthermore, acquiring the current contrast and tissue image pair includes acquiring the current contrast image and the current tissue image simultaneously or near-simultaneously in a manner that the current contrast image and the current tissue image are automatically registered with one another, further wherein the ROI or VOI defined in the current tissue image outlines the same ROI or VOI in the current contrast image.

According to yet another embodiment, the method further comprises repeating the steps of acquiring a next contrast and tissue image pair, establishing frame-to-frame registration between the next current tissue image and the baseline tissue image, using the frame-to-frame registration between the next current tissue image frame and the baseline tissue image frame to transfer the ROI or VOI from (i) the baseline contrast image to (ii) the next contrast image, thereby creating a transformed ROI or VOI in the next current contrast image, and performing quantitative analysis on the transformed ROI or VOI of the next current contrast image. In addition, the method includes integrating CEUS quantitative analysis with at least one selected from the group consisting of additional diagnosis procedures, therapy procedures, and providing target information, navigation, and guidance for an interventional procedure and/or a localized therapy.

In one embodiment, the steps of (i) acquiring a next contrast and tissue image pair, (ii) establishing frame-to-frame registration, and (iii) using the frame-to-frame registration between the current tissue image frame and the baseline tissue image frame to transfer the ROI or VOI from the baseline contrast image to the current contrast image together comprise an image-based registration that automatically compensates for tissue motion in the current contrast image which may have occurred between acquisition of the initial baseline contrast image and the current contrast image. Automatic compensation for tissue motion occurs in real time using the image-based registration.

According to another embodiment, the method further includes acquiring the current contrast and tissue image pair which comprise an $i^{th}$ contrast image and an $i^{th}$ tissue image. Establishing the frame-to-frame registration includes determining a ROI or VOI motion transformation $T_i$ from the baseline image to the $i^{th}$ tissue image. In addition, the motion transformation $T_i$ is determined as a function of registering image information within the ROI or VOI of the baseline image to the $i^{th}$ tissue image. $T_i$ is a transformation describing a corresponding translation and rotation. The method uses the frame-to-frame registration to transfer the ROI or VOI, and comprises applying the transformation $T_i$ to transform the baseline contrast image ROI or VOI into $ROI^i$ or $VOI^i$, respectively, of the $i^{th}$ contrast image frame.

In yet another embodiment, the method further comprises integrating the steps of acquiring the initial and next ultrasound contrast and tissue image pairs with a position tracking system. In addition, the method further comprises measuring at least one of a position and an orientation of an ultrasound probe with the tracking system and using the measured position/orientation to more closely align the ROI or VOI in the baseline tissue image and $i^{th}$ tissue image frames and to provide an improved starting point for image-based frame-to-frame registration between them. Still further, the method comprises eliminating a rotational component of the ultrasound probe motion using probe tracking, wherein image-based registration is further confined to three degrees of freedom (3 DOF) corresponding to translation in a coordinate system of (x,y,z) instead of six degrees of freedom (6 DoF) corresponding to translation and rotation in a coordinate system (x,y,z,θx,θy,θz).

In a still further embodiment, the method includes simultaneously processing tracking position information from the tracking system with an image stream from an ultrasound scanner, wherein the ultrasound scanner is configured to acquire the initial and $i^{th}$ tissue and contrast image frames. A pose $T_{base}$ of the ultrasound probe is stored during baseline image acquisition, and for each subsequent $i^{th}$ tissue image, the pose difference $T_{base}{}^i$ between an $i^{th}$ tissue image frame and the baseline tissue image is computed. The pose difference $T_{base}{}^i$ is used to determine $T_i^o$, corresponding to a ROI or VOI pose difference in the $i^{th}$ tissue image frame compared to ROI of the baseline tissue image frame under the assumption of no tissue motion, wherein any apparent motion is introduced solely by moving the probe relative to the tissue. Lastly, the pose difference $T_i^o$ is used as a starting position for an image-based registration process for determining a ROI or VOI motion transformation $T_i$ from the baseline tissue image to the $i^{th}$ tissue image, wherein the motion transformation $T_i$ is determined as a function of registering image information within the ROI or VOI of the baseline image to the $i^{th}$ tissue image.

According to yet another embodiment, performing quantitative analysis of image contents within the $ROI^i$ or $VOI^i$ of the $i^{th}$ contrast image frame includes generating quantitative results. The method further comprises analyzing a time series of quantitative results obtained from individual ones of a plurality of subsequent acquired $i^{th}$ contrast image frames to determine parameters that can provide diagnostic information. In addition, the quantitative analysis includes computing mean and standard deviation of brightness, and the parameters include tissue perfusion constants.

Still further, an ultrasound scanner apparatus is configured to implement quantitative 3D contrast enhanced ultrasound (CEUS) analysis according to the various embodiments of the method of the present disclosure.

As discussed herein, the embodiments of the present disclosure relate to enabling automatic quantification of volumetric ultrasound contrast images, allowing the creation of "parametric" images that contain information extracted from "raw" contrast image by means of image processing. The methods according to the embodiments of the present disclosure advantageously overcome prior methods for creation of such parametric images which were tedious because of image motion artifacts. The embodiments of the present disclosure advantageously compensate for tissue motion automatically.

The embodiments of the present disclosure further include a spatial tracking system, which adds robustness to the image processing method of the embodiment absent the spatial tracking system. In addition, the spatial tracking system can be further used to integrate the resulting "parametric" image with an image guidance system, wherein the "parametric" (as opposed to the "raw" contrast image) contrast image can be used to provide diagnostic information for guidance during an intervention or therapy.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be applied to contrast-enhanced ultrasound imaging studies. In particular, the invention can integrate diagnosis and therapy by providing target information and guidance for biopsy and therapeutic procedures. In addition, the ultrasound scanner and workstation can also comprise a single unit configured to implement the various aspects of the method of CEUS quantitative analysis as described herein. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:
1. A method for quantitative 3D contrast enhanced ultrasound (CEUS) analysis, comprising:
    acquiring (54) an initial ultrasound contrast image and an initial tissue image pair for a desired portion of a given anatomy;

establishing (56) one of a region of interest (ROI) or volume of interest (VOI) in the acquired initial tissue image, wherein the corresponding tissue image becomes a baseline tissue image;

automatically registering (58) the established ROI or VOI from the initial tissue image to the initial contrast image, wherein the corresponding contrast image becomes a baseline contrast image;

performing quantitative analysis (60) on the ROI or VOI of the baseline contrast image;

acquiring (62) a next ultrasound contrast image and tissue image pair, corresponding to an $i^{th}$ current contrast image and tissue image pair;

establishing frame-to-frame registration (64) between (i) the current tissue image and (ii) the baseline tissue image;

using the frame-to-frame registration (66) between the current tissue image frame and the baseline tissue image frame to transfer the ROI or VOI from (i) the baseline contrast image to (ii) the current contrast image, the current contrast and tissue image pair comprising an $i^{th}$ contrast image and an $i^{th}$ tissue image, establishing the frame-to-frame registration including determining a ROI or VOI motion transformation $T_i$ from the baseline image to the $i^{th}$ tissue image, the motion transformation $T_i$ being determined as a function of registering image information within the ROI or VOI of the baseline image to the $i^{th}$ tissue image, thereby creating a transformed ROI or VOI in the current contrast image; and performing quantitative analysis (68) on the transformed ROI or VOI of the current contrast image.

2. The method of claim 1, wherein the initial contrast and tissue image pair may comprise any image pair selected for purposes of the quantitative CEUS analysis as an initial image pair, which does not necessarily imply that the image pair has to comprise the first image pair obtained.

3. The method of claim 1, wherein establishing the ROI or VOI in the initial acquired tissue image comprises manually identifying the ROI or VOI within the baseline tissue image.

4. The method of claim 1, wherein the step of acquiring the initial contrast and tissue image pair includes acquiring the contrast image and the tissue image simultaneously or near-simultaneously in a manner that the contrast and tissue images are automatically registered with one another.

5. The method of claim 4, further wherein the ROI or VOI defined in the baseline tissue image outlines the same ROI or VOI in the baseline contrast image.

6. The method of claim 1, wherein acquiring the current contrast and tissue image pair includes acquiring the current contrast image and the current tissue image simultaneously or near-simultaneously in a manner that the current contrast image and the current tissue image are automatically registered with one another, further wherein the ROI or VOI defined in the current tissue image outlines the same ROI or VOI in the current contrast image.

7. The method of claim 1, further comprising:
repeating the steps of acquiring a next contrast and tissue image pair, establishing frame-to-frame registration between the next current tissue image and the baseline tissue image, using the frame-to-frame registration between the next current tissue image frame and the baseline tissue image frame to transfer the ROI or VOI from (i) the baseline contrast image to (ii) the next contrast image, thereby creating a transformed ROI or VOI in the next current contrast image, and performing quantitative analysis on the transformed ROI or VOI of the next current contrast image.

8. The method of claim 7, further comprising:
integrating CEUS quantitative analysis with at least one selected from the group consisting of additional diagnosis procedures, therapy procedures, and providing target information, navigation, and guidance for at least one of an interventional procedure or a localized therapy.

9. The method of claim 1, wherein the steps of (i) acquiring a next contrast and tissue image pair, (ii) establishing frame-to-frame registration, and (iii) using the frame-to-frame registration between the current tissue image frame and the baseline tissue image frame to transfer the ROI or VOI from the baseline contrast image to the current contrast image together comprise an image-based registration that automatically compensates for tissue motion in the current contrast image which may have occurred between acquisition of the initial baseline contrast image and the current contrast image.

10. The method of claim 9, wherein the automatic compensation for tissue motion occurs in real time using the image-based registration.

11. The method of claim 1, wherein acquiring the initial contrast and tissue image pair comprises acquiring the tissue image prior to acquiring of the contrast image.

12. The method of claim 1, wherein $T_i$ is a transformation describing a corresponding translation and rotation, further wherein using the frame-to-frame registration to transfer the ROI or VOI comprises applying the transformation $T_i$ to transform the baseline contrast image ROI or VOI into $ROI^i$ or $VOI^i$, respectively, of the $i^{th}$ contrast image frame.

13. The method of claim 1, further comprising:
integrating the steps of acquiring the initial and next ultrasound contrast and tissue image pairs with a position tracking system.

14. The method of claim 13, further comprising:
measuring at least one of a position and an orientation of an ultrasound probe with the tracking system and using the measured position/orientation to more closely align the ROI or VOI in the baseline tissue image and $i^{th}$ tissue image frames and to provide an improved starting point for image-based frame-to-frame registration between them.

15. The method of claim 14, further comprising:
eliminating a rotational component of the ultrasound probe motion using probe tracking, wherein image-based registration is further confined to three degrees of freedom (3 DOF) corresponding to translation in a coordinate system of (x,y,z) instead of six degrees of freedom (6 DoF) corresponding to translation and rotation in a coordinate system (x,y,z,θx,θy,θz).

16. The method of claim 15, further comprising:
simultaneously processing tracking position information from the tracking system with an image stream from an ultrasound scanner, wherein the ultrasound scanner is configured to acquire the initial and $i^{th}$ tissue and contrast image frames;

storing a pose $T_{base}$ of the ultrasound probe during baseline image acquisition, and for each subsequent $i^{th}$ tissue image, computing the pose difference $T_{base}^{i}$ between an $i^{th}$ tissue image frame and the baseline tissue image;

using the pose difference $T_{base}^{i}$ to determine $T_i^0$, corresponding to a ROI or VOI pose difference in the $i^{th}$ tissue image frame compared to ROI of the baseline tissue image frame under the assumption of no tissue motion, wherein any apparent motion is introduced solely by moving the probe relative to the tissue; and using the pose difference $T_i^0$ as a starting position for an image-based registration process for determining a ROI or VOI motion transformation $T_i$ from the baseline tissue image to the i$^{th}$ tissue image, wherein the motion transformation $T_i$ is determined as a function of registering image information within the ROI or VOI of the baseline image to the i$^{th}$ tissue image.

17. The method of claim 1, wherein performing quantitative analysis of image contents within the ROI$^i$ or VOI$^i$ of the i$^{th}$ contrast image frame includes generating quantitative results, the method further comprising:
   analyzing a time series of quantitative results obtained from individual ones of a plurality of subsequent acquired i$^{th}$ contrast image frames to determine parameters that can provide diagnostic information.

18. The method of claim 17, wherein the quantitative analysis includes computing mean and standard deviation of brightness, and wherein the parameters include tissue perfusion constants.

19. An ultrasound scanner apparatus configured to implement quantitative 3D contrast enhanced ultrasound (CEUS) analysis according to the method of claim 1.

* * * * *